US011702376B2

(12) United States Patent
Abdel Shahid et al.

(10) Patent No.: US 11,702,376 B2
(45) Date of Patent: *Jul. 18, 2023

(54) 5G AVOIDANCE DURING LTE-BASED REAL-TIME COMMUNICATIONS

(71) Applicant: T-Mobile USA, Inc., Bellevue, WA (US)

(72) Inventors: Wafik Abdel Shahid, Kenmore, WA (US); Ming Shan Kwok, Seattle, WA (US)

(73) Assignee: T-Mobile USA, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,150

(22) Filed: Dec. 22, 2021

(65) Prior Publication Data

US 2022/0112143 A1 Apr. 14, 2022

Related U.S. Application Data

(63) Continuation of application No. 16/696,375, filed on Nov. 26, 2019, now Pat. No. 11,212,859.

(51) Int. Cl.
*H04W 76/16* (2018.01)
*C07C 2/32* (2006.01)

(52) U.S. Cl.
CPC .......... *C07C 2/32* (2013.01); *C07C 2527/128* (2013.01); *C07C 2531/02* (2013.01);
(Continued)

(58) Field of Classification Search
CPC ..... H04W 76/16; H04W 76/22; H04W 76/34; H04W 88/10
(Continued)

(56) References Cited

U.S. PATENT DOCUMENTS

2020/0008069 A1 1/2020 Zhu et al.
2020/0015303 A1 1/2020 Tsai et al.
(Continued)

FOREIGN PATENT DOCUMENTS

EP 3769565 A1 1/2021
EP 3780757 A1 2/2021
(Continued)

OTHER PUBLICATIONS

The Extended European Search Report dated Apr. 22, 2021 for European Patent Application No. 20207838.2, 9 pages.
(Continued)

*Primary Examiner* — Robert J Lopata
(74) *Attorney, Agent, or Firm* — Lee & Hayes, P.C.

(57) ABSTRACT

A radio access network (RAN) configured to support real-time communications over a Long-Term Evolution (LTE) connection is described herein. When a request for a data transmission is received and a real-time communication session over the LTE connection is established, the RAN utilizes the LTE connection, not a New Radio (NR) connection, for the data transmission. When a request for a further real-time communication is received and there is an active data transmission session over the NR connection, the RAN performs at least one of ceasing to allocate traffic to the NR connection for downlink or reconfiguring the data transmission session to send data over the LTE connection.

20 Claims, 5 Drawing Sheets

(52) U.S. Cl.
CPC ...... *C07C 2531/04* (2013.01); *C07C 2531/14* (2013.01); *C07C 2531/22* (2013.01); *C07C 2531/28* (2013.01)

(58) Field of Classification Search
USPC .......................................................... 370/329
See application file for complete search history.

(56) References Cited

U.S. PATENT DOCUMENTS

| | | | |
|---|---|---|---|
| 2020/0068647 A1* | 2/2020 | Jha | H04W 60/005 |
| 2020/0100309 A1* | 3/2020 | Jha | H04W 48/18 |
| 2020/0106663 A1* | 4/2020 | Yoo | H04L 67/10 |
| 2020/0187043 A1 | 6/2020 | Xin et al. | |
| 2020/0275259 A1 | 8/2020 | Zhu et al. | |
| 2020/0296638 A1 | 9/2020 | Tsai et al. | |
| 2020/0314702 A1 | 10/2020 | Rahman | |
| 2020/0336979 A1 | 10/2020 | Aoyagi et al. | |
| 2020/0351771 A1 | 11/2020 | Geekie et al. | |
| 2020/0383010 A1 | 12/2020 | Zhu et al. | |
| 2020/0413314 A1 | 12/2020 | Wang | |
| 2021/0022073 A1 | 1/2021 | Kwok et al. | |
| 2021/0029773 A1 | 1/2021 | Majumder et al. | |
| 2021/0045020 A1* | 2/2021 | Youtz | H04W 76/38 |
| 2021/0051530 A1 | 2/2021 | Venkataraman et al. | |
| 2021/0084543 A1 | 3/2021 | Wang et al. | |
| 2021/0160945 A1 | 5/2021 | Abdel Shahid et al. | |
| 2021/0282059 A1* | 9/2021 | Li | H04M 7/0057 |
| 2021/0298106 A1* | 9/2021 | Jha | H04W 76/16 |
| 2022/0248278 A1* | 8/2022 | Huang | H04W 36/00837 |
| 2022/0248488 A1* | 8/2022 | Sen | H04B 17/318 |

FOREIGN PATENT DOCUMENTS

| | | |
|---|---|---|
| EP | 3782429 A1 | 2/2021 |
| WO | WO2020017886 A1 | 1/2020 |
| WO | WO2020040546 A1 | 2/2020 |

OTHER PUBLICATIONS

Office Action for U.S. Appl. No. 16/696,375, dated May 4, 2021, Shahid, "5G Avoidance During LTE-Based Real-Time Communications", 8 pages.

* cited by examiner

5G AVOIDANCE DURING LTE-BASED REAL-TIME COMMUNICATIONS

CROSS REFERENCE TO RELATED APPLICATIONS

The present disclosure is a continuation of, and claims priority under 35 U.S.C. § 120 to, U.S. patent application Ser. No. 16/696,375 filed Nov. 26, 2019, the disclosure of which is hereby incorporated by reference in its entirety.

BACKGROUND

Concurrent transmission of voice, video, or other real-time communications along with control messaging, such as radio resource control (RRC) reconfiguration messages can negatively impact the quality of the voice, video, or other real-time communications. When a radio access network (RAN) provides, for example, voice or video services over a Long-Term Evolution (LTE) connection and provides data transmission separately over a New Radio (NR) connection, the characteristics of NR connections may lead to increased RRC reconfiguration messaging. Networks offering LTE connections are often referred to as fourth generation (4G) networks, and network offering NR connections are often referred to as fifth generation (5G) networks.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

When a RAN receives a request for a data transmission and a real-time communication session over an LTE connection is already established, the RAN utilizes the LTE connection, not a NR connection, for the data transmission. Additionally, when a request for a further real-time communication is received and there is an active data transmission session over the NR connection, the RAN may cease allocating traffic to the NR connection for downlink. Also, or instead, the RAN may reconfigure the data transmission session to send data over the LTE connection.

In various implementations, the RAN may perform a series of operations responsive to receiving a request for a data transmission session. First, upon receiving the request for a data transmission session, the RAN may determine if A) a real-time communication session is established and B) a NR connection between the RAN and the request-making user equipment (UE) is absent or idle. If the answer to A) and B) is "yes," the RAN may utilize a LTE connection between the RAN and UE to support the data transmission session. If the answer to either A) or B) is "no", the RAN may utilize the NR connection to support the data transmission session.

The RAN may also be configured to take one of two different approaches to handling a request for a real-time communication. Under a first approach, upon receiving a request for a real-time communication session, the RAN may determine if a data transmission session over a NR connection is active. If the data transmission session over the NR connection is active, the RAN may cease allocating traffic to the NR connection for downlink and, following that, may establish the real-time communication session over a LTE connection. As a result of ceasing to allocate traffic to the NR connection, the NR connection will eventually be released. Alternatively, before that release happens, the RAN may reconfigure the data transmission session to utilize the LTE connection. Further, in some implementations, after determining that the data transmission session is active, the RAN may determine if a data transmission buffer size is less than a threshold. If less than the threshold, the RAN may perform the ceasing, as described above. If the data transmission buffer size meets or exceeds the threshold, the RAN may instead reconfigure the data transmission session to utilize the LTE connection.

Under a second of the two different approaches, upon receiving the request for a real-time communication session, the RAN may determine if a data transmission session over a NR connection is active. If the data transmission session over the NR connection is active, the RAN may reconfigure the data transmission session to utilize a LTE connection and, following that, may establish the real-time communication session over the LTE connection.

Overview

Figure 1A:
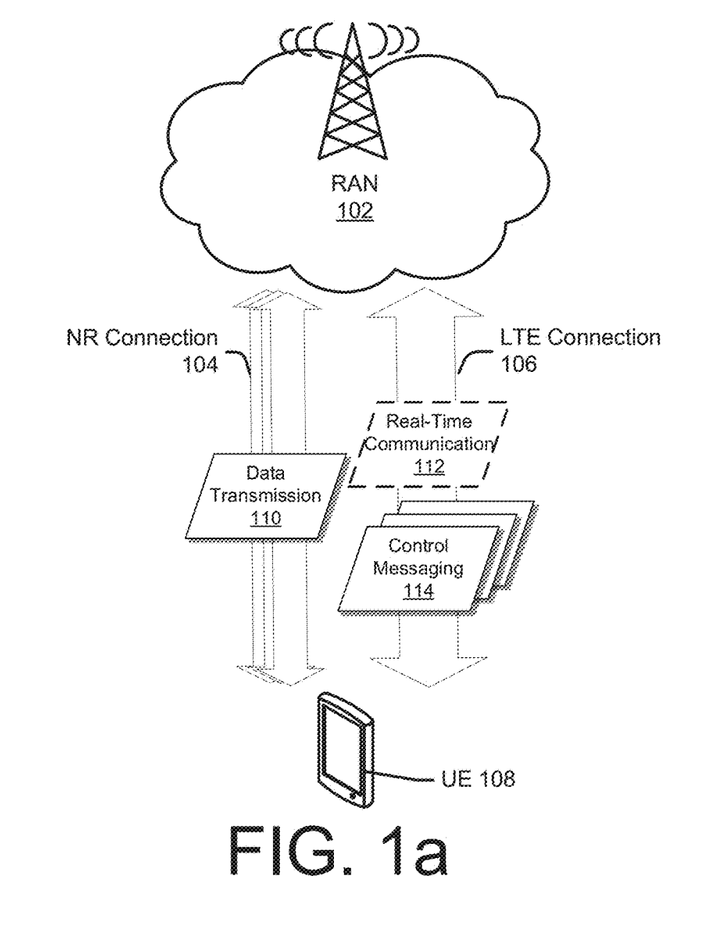
FIGS. 1a-1b illustrate an example overview of a RAN configured to avoid impact of control messaging on real-time communications.
Figure 1B:
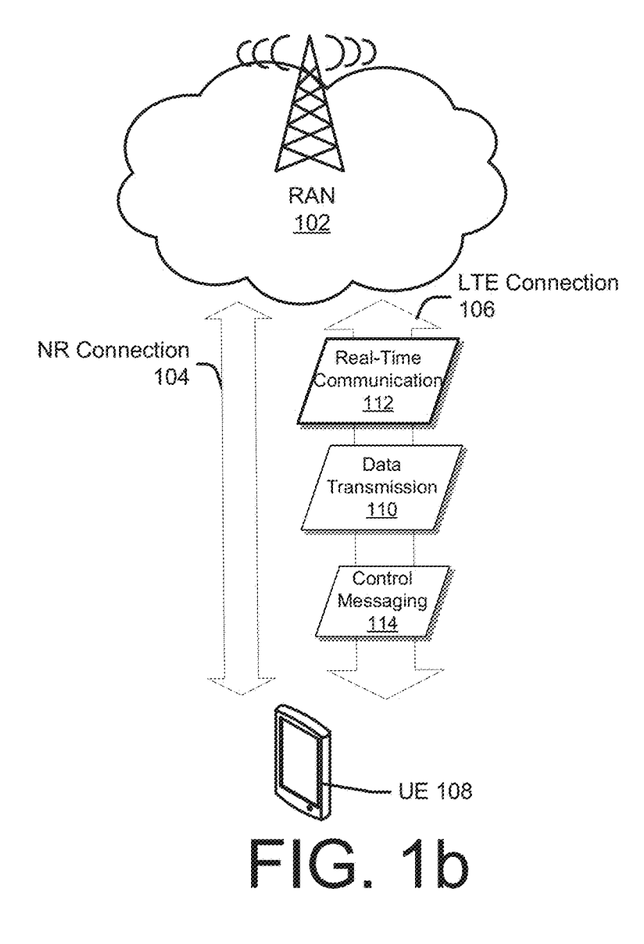

FIGS. 1a-1b illustrate an example overview of a RAN configured to avoid impact of control messaging on real-time communications. As illustrated in FIG. 1a, a RAN 102 may have both a NR connection 104 and a LTE connection 106 with a UE 108. The NR connection 104 may be used for data transmissions 110, and the LTE connection 106 may be used for real-time communications 112, as well as control messaging 114. The use of the NR connection 104 for the data transmissions 110 results in a volume of control messaging 114 that impacts the quality of the real-time communications 112. In FIG. 1b, data transmissions 110 are switched to the LTE connection 106 when real-time communications 112 are established, resulting in a reduced volume of control messaging 114.

In various implementations, the RAN 102 may be one of a number of localized access networks of a telecommunication network, the telecommunication network providing connectivity to UEs, such as UEs subscribing to the telecommunication network and visiting UEs, both for communications and for data publishing and consumption. Such communications may include voice calling, video calling, text messaging, multimedia messaging, conferencing, etc. Data publishing and consumption may include streaming of video, voice, images, etc., browsing of network content, participation in social media, participation in online games, etc. UE 108 may connect to RAN 102, which in turn may connect to a remote UE, computing device, or service via the telecommunication network and, in some examples, one or more other networks.

In addition to the RAN 102, the telecommunication network may include a core network and one or more other RANs. Example access networks may utilize any Third Generation Partnership Project (3GPP) Standard 3G, 4G, 5G, etc. technology or other 3G, 4G, 5G, etc. technology. Alternatively or additionally, example access networks may include unlicensed wireless networks, such as WiFi® or WiMax® networks, and/or wired access networks. An example core network may be a packet-based network and may support legacy, circuit-switched connections. The core network may also include 3GPP Internet Protocol (IP) Multimedia Subsystem (IMS) technology in support of packet-based communications. Such 3GPP IMS technology may support communications made using the Session Initiation Protocol (SIP).

As illustrated in FIGS. 1a-1b, the RAN 102 may include a cell tower; one or more base station units coupled to the cell tower, offering connectivity to cell areas of varying sizes, and using various technology types; one or more power sources; and mechanisms for connecting the base station unit(s) to the core network.

For example, the RAN 102 may include at least an eNode B (eNB) base station for supporting the LTE connection 106 and a gNode B (gNB) base station for supporting the NR connection 104. The eNB and gNB may be implemented in a single computing device or through multiple computing devices and may represent an ENDC (E-UTRAN (Evolved UNITS (Universal Mobile Telecommunications Service) Terrestrial Radio Access Network) New Radio-Dual Connectivity) solution. The ENDC solution enables the UE 108 to connect to the eNB through the LTE connection 106, with the eNB serving as a master node, and to the gNB through the NR connection 104, with the gNB serving as a secondary node. ENDC solutions are specified in greater detail by 3GPP standards.

Figure 5:
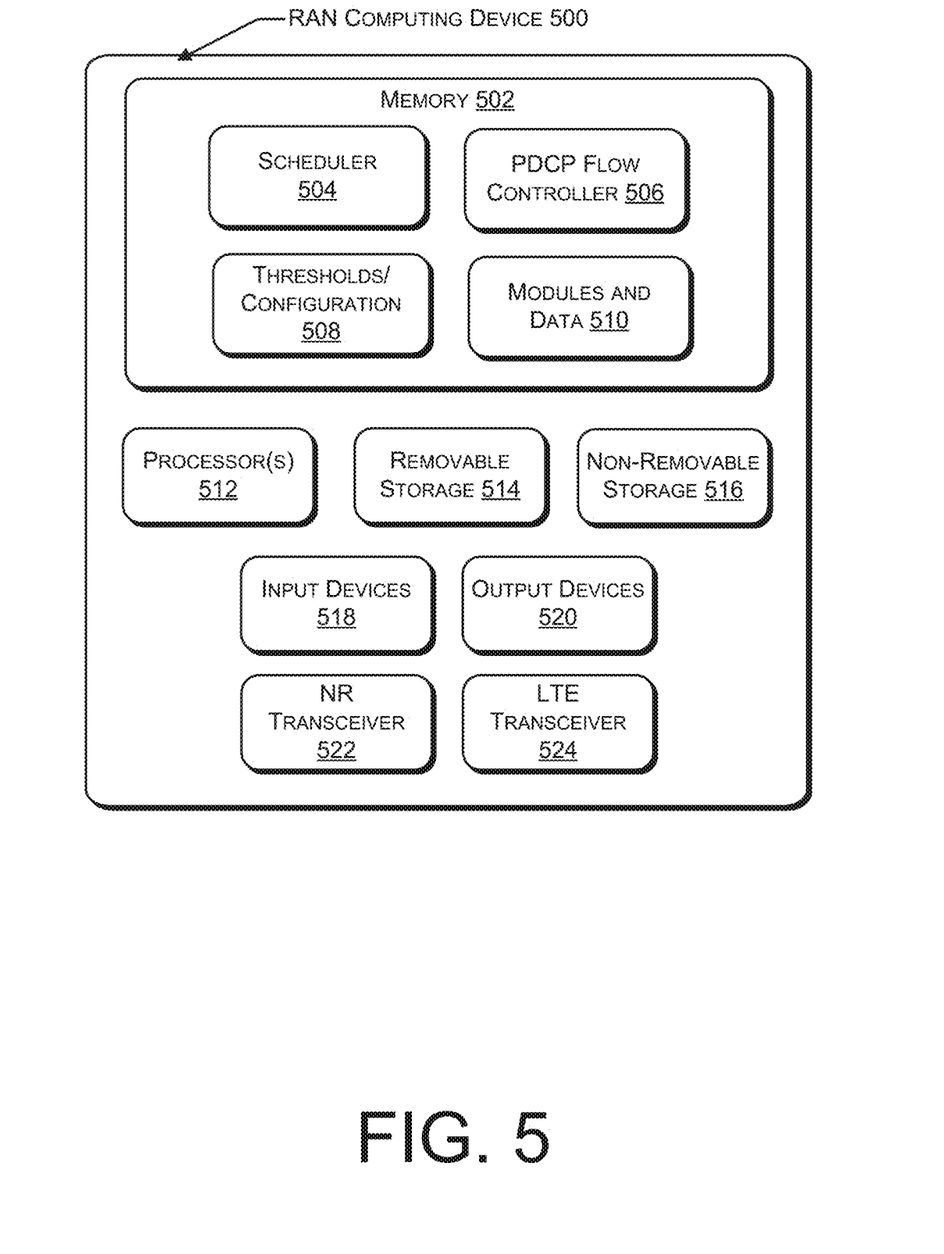
FIG. 5 illustrates an example architecture of a computing device of a RAN.

Each base station may also include a scheduler to allocate channels of frequency bands or time slots for frequency bands, as well as a PDCP (Packet Data Convergence Protocol) flow controller. Further, the computing device implementing the gNB may include at least a NR transceiver to support the NR connection 104, and the computing device implementing the eNB may include at least a LTE transceiver to support the LTE connection 106. An example computing device configured to implement a eNB and gNB of the RAN 102 is illustrated in FIG. 5 and described further herein with reference to that figure.

In various implementations, the UE 108 may be any sort of wireless communication device, such as a cellular handset, a tablet computer, a personal computer, a desktop computing device, a media player, etc. The UE 108 may include one or more radios for wireless communication and/or wired port(s), may include both input and output components, and may have a Subscriber Identity Module (SIM) or other technology that securely stores identity information for the UE 108. In a single radio implementation, the radio may be capable of communicating with both the eNB and gNB of the RAN 102 through the LTE connection 106 and the NR connection 104, respectively. In dual radio implementations, one radio of the UE 108 may be used to communicate with the gNB over the NR connection 104, and the other radio of the UE 108 may be used to communicate with the eNB over the LTE connection 106. Via the radio(s), its platform, and one or more applications, the UE 108 may engage in data transmissions 110, real-time communications 112, and control messaging 114.

In some implementations, the LTE connection 106 may involve multiple frequency bands and multiple bearers, with separate bearers for real-time communications 112 and for data transmissions (such as, e.g., data transmissions 110, as shown in FIG. 1b). Control messaging 114 may be transmitted using either bearer. While the NR connection 104 could similarly support multiple bearers, NR connections, such as NR connection 104, are often used only for data transmissions, such as data transmission 110. This limited use reflects the characteristics associated with the spectrum utilized for NR connections, such as shorter range and greater susceptibility to interference.

As noted herein, the data transmission 110 may be part of any data transmission session and may involve any one or more of streaming of video, voice, images, etc., browsing of network content, participation in social media, or participation in online games, among others. The real-time communications 112 may be part of any data service, such as voice over LTE (VoLTE) or video over LTE (ViLTE). Control messaging 114, as mentioned, may include RRC reconfiguration messages for establishing or releasing the radio bearer for the NR connection 104.

In various implementations, as illustrated in FIG. 1a, the use of the NR connection 104 for data transmission 110 results in a higher volume of control messaging 114. The higher volume of control messaging 114 may reflect difficulties that the UE 108 experiences with the NR connection 104, such as frequent loss of connectivity, packet loss, etc. Responsive to these conditions, the UE 108 may send control messages 114, such as RRC reconfiguration messages, via the LTE connection 106 requesting that the RAN 102 establish or release the bearer corresponding to the NR connection 104. These control messages 114 in turn impact the quality of the real-time communication 112 supported by the LTE connection 106

FIG. 1b, in contrast, illustrates a RAN 102 configured to reduce the control messaging 114 transmitted over the LTE connection 106 during real-time communications 112. To reduce the control messaging 224, the RAN 102 utilizes the LTE connection 106 for the data transmission 110. The RAN 102 utilizes the LTE connection 106 to service new requests for data transmission that are received when a real-time communication 112 is established. And when a data transmission 110 over the NR connection 104 is active and a request for real-time communication 112 is received, the RAN 102 performs at least one of ceasing to allocate traffic to downlink for the NR connection 104 or reconfiguring the data transmission 110 to utilize the LTE connection 106.

For example, upon receiving a data transmission request from a UE 108, the RAN 102 may first determine if A) a real-time communication 112 is currently established and B) the NR connection 104 is absent or idle. If the answer to A) and B) is "yes," the RAN 102 may utilize the LTE connection 106 to support the data transmission 110. This may involve establishing a data bearer for the LTE connection 106 or utilizing an existing bearer. If the answer to either A) or B) is "no", the RAN 102 may utilize the NR connection 104 to support the data transmission 110.

Further, upon receiving a real-time communication request from the UE 108, the RAN 102 may determine if a data transmission 110 over the NR connection 110 is active. If the data transmission 110 over the NR connection 104 is active, a PDCP flow controller of the RAN 102 may cease allocating traffic to the NR connection 104 for downlink and, following that, the RAN 102 may establish the real-time communication 112 over the LTE connection 106. As a result of ceasing to allocate traffic to the NR connection 104, the NR connection 104 will eventually be released by the RAN 102. Alternatively, before that release happens, the RAN 102 may reconfigure the data transmission 110 to utilize the LTE connection 106. Further, in some implementations, after determining that the data transmission 110 is active, the RAN 102 may determine if a data transmission buffer size is less than a threshold. If less than the threshold, the RAN 102 may perform the ceasing, as described above. If the data transmission buffer size meets or exceeds the threshold, the RAN 102 may instead reconfigure the data transmission 110 to utilize the LTE connection 106. While reconfiguring the data transmission 110 to utilize the LTE connection 106 may involve control messaging 114, the result of the change—data transmission 110 over the LTE connection 106—will mean a lower overall volume of control messaging, as the NR connection 104 will no longer be supporting the data transmission 110.

Alternatively, upon receiving a request for a real-time communication 112 from the UE 108, the RAN 102 may determine if a data transmission 110 over a NR connection is active and, if active, the RAN may reconfigure the data transmission 110 to utilize the LTE connection 106. This reconfiguration may happen right after making the determination to ensure a minimum of control messaging 114. Following that, the RAN 102 may establish the real-time communication 112 over the LTE connection 106.

Example Operations

Figure 2:
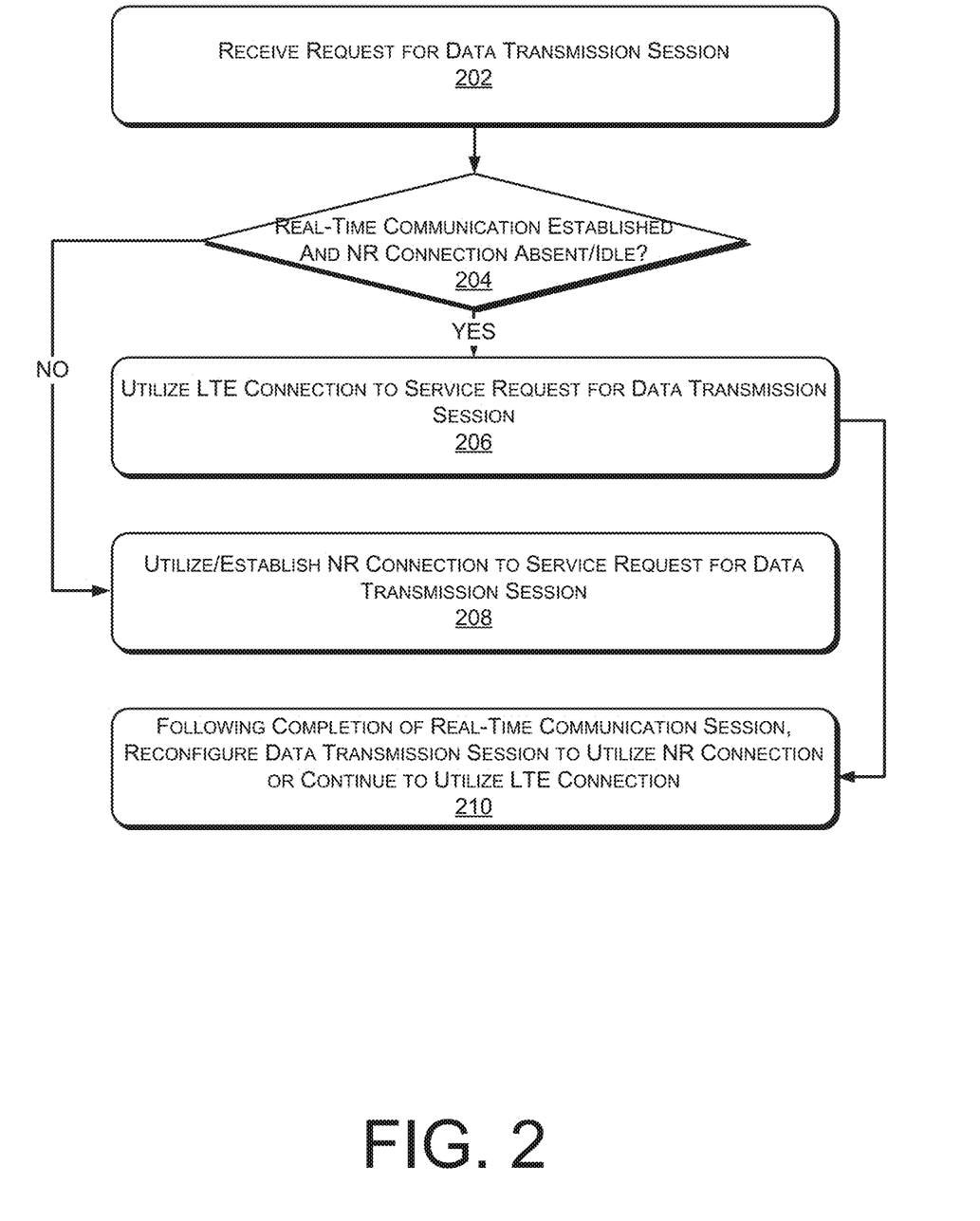
FIG. 2 illustrates a flow chart of an example process for handling a request for a data transmission received during an established real-time communication session.
Figure 3:
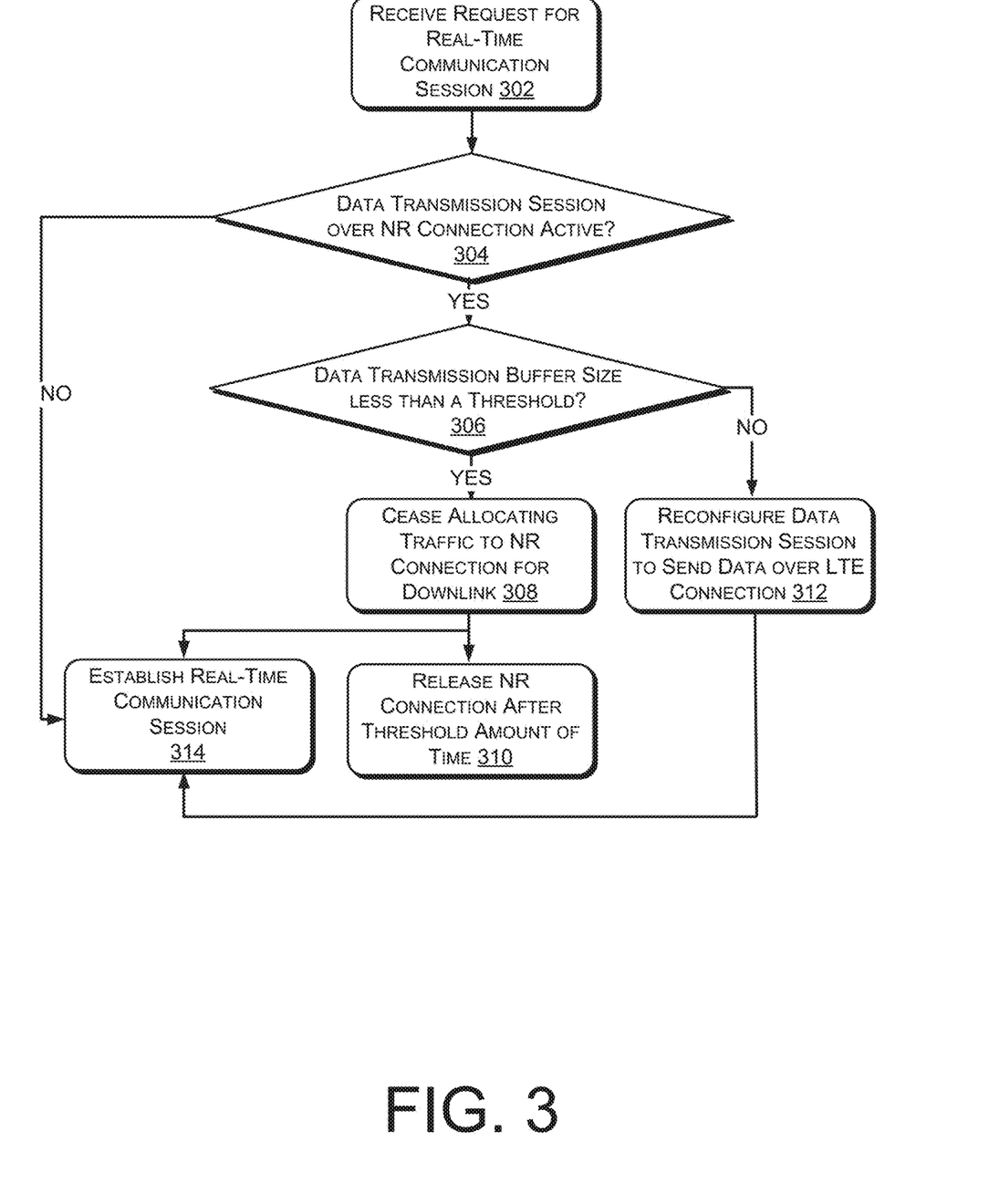
FIG. 3 illustrates a flow chart of one example process for handling a request for a real-time communication received while a data transmission session is active.
Figure 4:
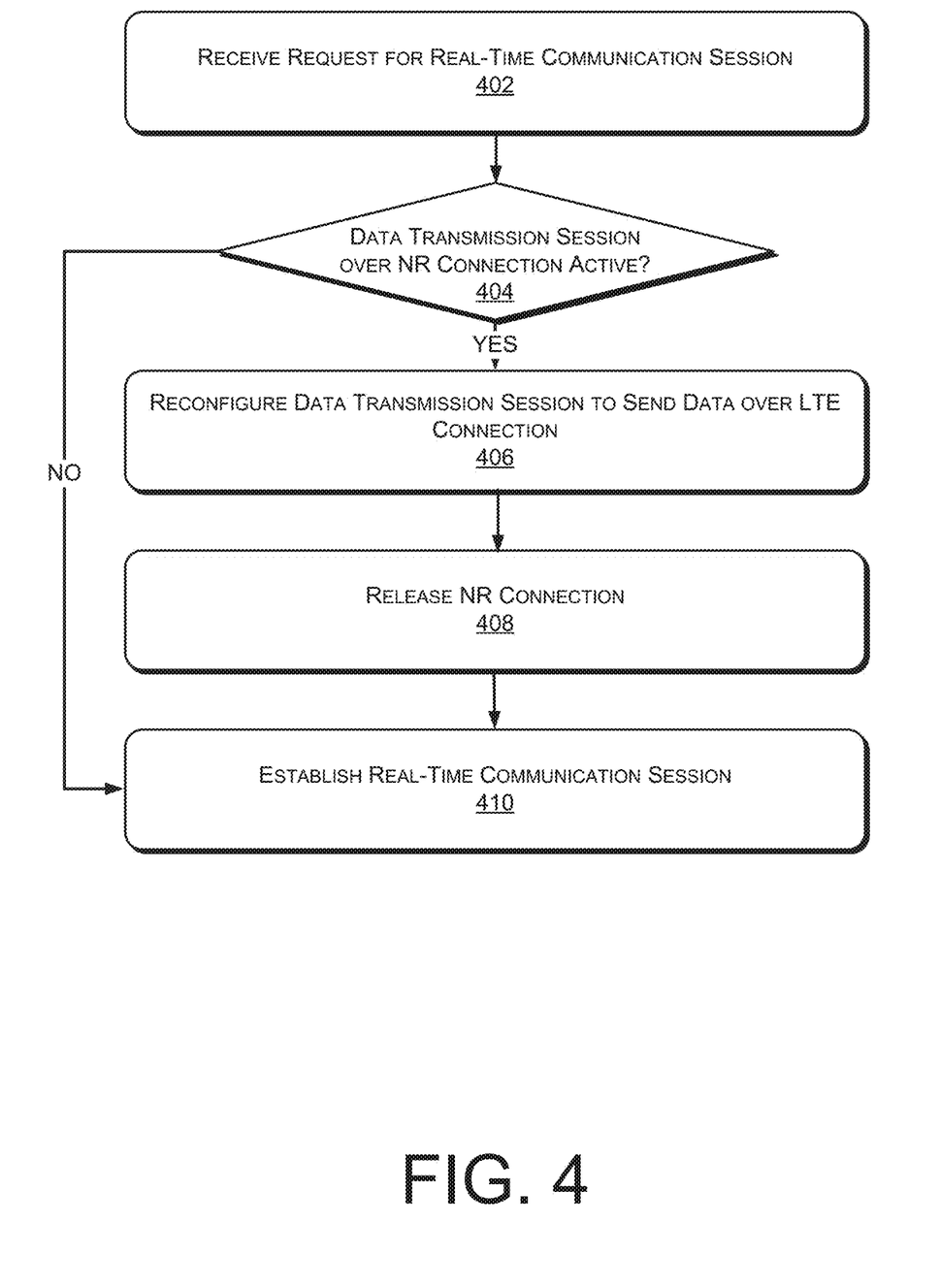
FIG. 4 illustrates a flow chart of another example process for handling a request for a real-time communication received while a data transmission session is active.

FIGS. 2-4 illustrate example processes. These processes are illustrated as logical flow graphs, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes.

FIG. 2 illustrates a flow chart of an example process for handling a request for a data transmission received during an established real-time communication session. As illustrated at 202, a RAN may receive a request for a data transmission session from, e.g., a UE.

At 204, the RAN may determine whether a real-time communication session is established, and at 206, the RAN may further determine whether a NR connection is absent or idle. In some examples, the real-time communication session is one of a VoLTE communication session or a ViLTE communication session and is supported by an LTE connection.

At 208, when the real-time communication session is established and the NR connection is absent or idle, the RAN may utilize an LTE connection to service the request. Alternatively, at 210, when the real-time communication session is not established or the NR connection is active, the RAN may utilize the NR connection to service the request or establish the NR connection to service the request.

At 212, following completion of the real-time communication session, the RAN may reconfigure the data transmission session to utilize the NR connection or may continue to utilize the LTE connection for the data transmission session.

FIG. 3 illustrates a flow chart of one example process for handling a request for a real-time communication received while a data transmission session is active. As illustrated, at 302, a RAN may receive a request to for a real-time communication session from, e.g., a UE.

At 304, upon receiving the request, the RAN may determine whether a data transmission session over the NR connection is active. If active, the RAN may proceed to further determine, at 306, whether a data transmission buffer size is less than a threshold. If the data transmission buffer size is less than a threshold, the RAN ceases, at 308, to allocate traffic to the NR connection for downlink. At 310, after performing the ceasing for a threshold amount of time, the RAN releases the NR connection.

At 312, if the data transmission buffer size meets or exceeds a threshold, the RAN reconfigures the data transmission session to send data over the LTE connection. In some examples, the reconfiguring at 312 may also be performed following the ceasing at 308.

At 314, the RAN may establish the real-time communication session after performing the reconfiguring at 312 or after the ceasing at 308. Also, when the RAN determines at 304 that the data transmission session over the NR connection is not active, the RAN may proceed to establish the real-time communication session at 314.

FIG. 4 illustrates a flow chart of another example process for handling a request for a real-time communication received while a data transmission session is active. As illustrated, at 402, a RAN may receive a request to for a real-time communication session from, e.g., a UE.

At 404, upon receiving the request, the RAN may determine whether a data transmission session over the NR connection is active.

At 406, upon determining that the data transmission session over the NR connection is active, the RAN may reconfigure the data transmission session to send data over the LTE connection. Such reconfiguration may happen a single time upon completion of the determining at 404. Further, at 408, after reconfiguring the data transmission session to send data over the LTE connection, the RAN may release the NR connection.

At 410, the RAN may establish the real-time communication session after performing the reconfiguring. Also, when the RAN determines at 404 that the data transmission session over the NR connection is not active, the RAN may proceed to establish the real-time communication session at 410.

Example Architecture

FIG. 5 illustrates an example architecture of a computing device of a RAN. The RAN may be an example of a RAN 102, which is described further herein. The computing device 500 can have a system memory 502. The system memory 302 can store a scheduler 504, a PDCP flow controller 506, threshold and/or configuration 508, and/or other modules and data 510. The computing device 500 can also include processor(s) 512, removable storage 514, non-removable storage 516, input device(s) 518, output device(s) 520, an NR transceiver 522, and an LTE transceiver 524.

In various examples, system memory 502 can be volatile (such as random-access memory (RAM)), non-volatile (such as read-only memory (ROM), flash memory, etc.), or some combination of the two. Example system memory 502 can include one or more of RAM, ROM, electronically erasable programmable ROM (EEPROM), a Flash Memory, a hard drive, a memory card, an optical storage, a magnetic cassette, a magnetic tape, a magnetic disk storage or another magnetic storage devices, or any other medium.

Examples of the scheduler 504, the PDCP flow controller 506, and the threshold and/or configuration 508 are described above in detail with reference to FIG. 1. As noted, these components may be involved in allocating data, allocating time slots, establishing and releasing radio bearers, among other functions.

The other modules and data 510 can be utilized by the computing device 500 to perform or enable performing any action taken by the computing device 500. The other modules and data 510 can include a platform and applications, and data utilized by the platform and applications.

In some embodiments, the processor(s) 512 can be a central processing unit (CPU), a graphics processing unit (GPU), both CPU and GPU, or other processing unit or component known in the art.

The computing device 500 can also include additional data storage devices (removable and/or non-removable) such as, for example, magnetic disks, optical disks, or tape. Such additional storage is illustrated in FIG. 5 by removable storage 514 and non-removable storage 516. Non-transitory computer-readable media may include volatile and nonvolatile, removable and non-removable media implemented in any method or technology for storage of information, such as computer readable instructions, data structures, program modules, or other data. System memory 502, removable storage 514 and non-removable storage 516 are all examples of non-transitory computer-readable media. Non-transitory computer-readable media include, but are not limited to, RAM, ROM, EEPROM, flash memory or other memory technology, compact disc-ROM (CD-ROM), digital versatile discs (DVD) or other optical storage, magnetic cassettes, magnetic tape, magnetic disk storage or other magnetic storage devices, or any other medium which can be used to store the desired information and which can be accessed by the computing device 500. Any such computer-readable storage media can be part of the computing device 500. In various examples, any or all of system memory 502, removable storage 514, and non-removable storage 516, store programming instructions which, when executed, implement some or all of the above-described operations of the computing device 500.

In some examples, the computing device 500 can also have input device(s) 518, such as a keyboard, a mouse, a touch-sensitive display, voice input device, etc., and/or output device(s) 520 such as a display, speakers, a printer, etc. These devices are well known in the art and need not be discussed at length here.

The computing device 500 can also include one or more transceiver, such as the NR transceiver 522 and the LTE transceiver 524 to facilitate communication with other devices, such as one or more UEs.

CONCLUSION

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:
1. A radio access network, comprising:
a processor;
a Long-Term Evolution (LTE) transceiver coupled to the processor and configured to send and receive at least real-time communications and data transmissions;
a new radio (NR) transceiver coupled to the process and configured to send and receive at least data transmissions; and
memory coupled to the processor and storing instructions that, when executed by the processor, cause the radio access network to perform operations comprising:
receiving a request for a real-time communication session;
upon receiving the request, determining whether a data transmission session over a new radio (NR) connection is active; and
when the data transmission session is active, ceasing to allocate traffic to the NR connection for downlink for a threshold amount of time.

2. The radio access network of claim 1, wherein the operations further comprise reconfiguring the data transmission session to send data over the NR connection for the downlink after ceasing to allocate the traffic to the NR connection for the downlink for the threshold amount of time.

3. The radio access network of claim 1, wherein the threshold amount of time comprises an amount of time sufficient to cause a release of the NR connection.

4. The radio access network of claim 1, wherein the operations further comprise reconfiguring the data transmission session to send data over an LTE connection after ceasing to allocate traffic to the NR connection for the downlink.

5. The radio access network of claim 1, wherein the operations further comprise establishing the real-time communication session after ceasing to allocate traffic to the NR connection for the downlink.

6. The radio access network of claim 5, wherein the operations further comprise reconfiguring the data transmission session to utilize the NR connection after completing the real-time communication session.

7. The radio access network of claim 1, wherein the operations further comprise, when the data transmission session is not active, utilizing the NR connection to service the request for the real-time communication session.

8. A method comprising:
receiving, by a radio access network (RAN), a request for a real-time communication session;
upon receiving the request, determining, by the RAN, whether a data transmission session over a new radio (NR) connection is active; and
when the data transmission session is active, ceasing, by the RAN, to allocate traffic to the NR connection for downlink for a threshold amount of time.

9. The method of claim 8, wherein the real-time communication session is one of a voice over Long-Term Evolution (VoLTE) communication session or a video over Long-Term Evolution (ViLTE) communication session.

10. The method of claim 8, further comprising utilizing a Long-Term Evolution (LTE) connection to service the request for the real-time communication session.

11. The method of claim 8, further comprising reconfiguring the data transmission session to send data over a Long-Term Evolution (LTE) connection after ceasing to allocate the traffic to the NR connection for the downlink for the threshold amount of time.

12. The method of claim 8, further comprising reconfiguring the data transmission session to send data over the NR connection after ceasing to allocate the traffic to the NR connection for the downlink for the threshold amount of time.

13. The method of claim 8, further comprising releasing the NR connection after ceasing to allocate the traffic to the NR connection for the downlink for a threshold amount of time.

14. The method of claim 8, further comprising, when the data transmission session is not active, utilizing the NR connection to service the request for the real-time communication session.

15. A non-transitory computer-readable medium having programming instructions stored thereon that, when executed by a computing device of a radio access network cause the radio access network to perform operations comprising:
  receiving, by a radio access network (RAN), a request to for a real-time communication session;
  upon receiving the request, determining, by the RAN, whether a data transmission session over a new radio (NR) connection is active; and
  when the data transmission session is active, ceasing, by the RAN, to allocate traffic to the NR connection for downlink for a threshold amount of time.

16. The non-transitory computer-readable medium of claim 15, wherein the operations further comprise, when the data transmission session is not active, utilizing a Long-Term Evolution (LTE) connection to service the request for the real-time communication session.

17. The non-transitory computer-readable medium of claim 16, wherein the operations further comprise reconfiguring the data transmission session to utilize the NR connection after completing the real-time communication session.

18. The non-transitory computer-readable medium of claim 15, wherein the operations further comprise reconfiguring the data transmission session to send data over the NR connection after ceasing to allocate the traffic to the NR connection for the downlink for the threshold amount of time.

19. The non-transitory computer-readable medium of claim 15, wherein the operations further comprise reconfiguring the data transmission session to send data over a Long-Term Evolution (LTE) connection after ceasing to allocate traffic to the NR connection for the downlink.

20. The non-transitory computer-readable medium of claim 19, wherein the operations further comprise releasing the NR connection and establishing the real-time communication session.

* * * * *